US005591841A

United States Patent [19]
Ji et al.

[11] Patent Number: 5,591,841
[45] Date of Patent: Jan. 7, 1997

[54] RAPID PURIFICATION OF CIRCULAR DNA BY TRIPLEX-MEDIATED AFFINITY CAPTURE

[76] Inventors: Huamin Ji, 4817 Sheboygan Ave.; Lloyd M. Smith, 1115 Amherst Dr., both of Madison, Wis. 53705

[21] Appl. No.: 317,102

[22] Filed: Sep. 30, 1994

Related U.S. Application Data

[63] Continuation of Ser. No. 4,374, Jan. 14, 1993, abandoned.

[51] Int. Cl.$^6$ .................................................. C07H 21/04
[52] U.S. Cl. .......................... 536/25.4; 435/6; 536/24.3
[58] Field of Search ............................... 536/25.4, 24.3; 435/6; 935/78

[56] References Cited

U.S. PATENT DOCUMENTS

| 5,176,996 | 1/1993 | Hogan et al. | 435/6 |
| 5,401,632 | 3/1995 | Wang et al. | 435/6 |

FOREIGN PATENT DOCUMENTS

| WO9006045 | 6/1990 | WIPO . |
| WO9006044 | 6/1990 | WIPO . |
| WO9006043 | 6/1990 | WIPO . |
| WO9006042 | 6/1990 | WIPO . |

OTHER PUBLICATIONS

Ji et al., *GATA* 11(2), 43–47 (1994).
Ji et al., *Analyt. Chem.* 65, 1323–1328 (1993 May 15).
Letai et al., *Biochemistry* 27, 9108–9112 (1988).
Sambrook et al., *Molecular Cloning*, Cold Spring Harbor Lab. Press, 1989.
Lyamichev et al., *Nucl. Acids Res.* 16(5), 2165–2178 (1988).
Arndt–Jovin et al., *Eur. J. Biochem.* 54, 411–418 (1975).

Beal and Dervan, "Second Structural Motif for Recognition of DNA by Oligonucleotide–Directed Triple–Helix Formation," *Science*, vol. 251:1360–1363 (1991).
Griffin and Dervan, "Recognition of Thymine–Adenine Base Pairs by Guanine in a Pyrimidine Triple Helix Motif," *Science*, vol. 245:967–971 (1989).
Ito, et al., "Affinity Capture Electrophoresis for Sequence–Specific DNA Purification," *GATA*, 9(3):96–99 (1992).
Ito, et al., "Sequence–specific DNA purification by triplex affinity capture," *Proc. Natl. Acad. Sci. USA*, vol. 89:495–498 (1992).
Takabatake, et al., "The use of purine–rich oligonucleotides in triplex–mediated DNA isolation and generation of unidirectional deletion," *Nucleic Acids Research*, vol. 20(21):5853–5854 (1992).
Vary, C. P. H., "Triple–Helical Capture Assay for Quantification of Polymerase Chain Reaction Products," *Clin. Chem.* 38/5:687–694 (1992).
Ito, et al., "Triplex affinity capture of a single copy clone from a yeast genomic library," *Nucleic Acids Research*, vol. 20(13):3524 (1992).

*Primary Examiner*—Kenneth R. Horlick
*Attorney, Agent, or Firm*— Quarles & Brady

[57] ABSTRACT

A single-step capture of a target supercoiled double-stranded DNA molecule is accomplished by forming a local triple-helix among two strands of the supercoiled circular DNA and an oligonucleotide probe. The oligonucleotide is bound to an immobilizing support which facilitates the immobilization and purification of target DNA molecules. Non-target DNA molecules and other contaminating cellular material are easily removed by washing. The triple-helical structure is destabilized by raising the pH, leaving purified target DNA in the supernatant and reusable affinity capture oligonucleotide secured to the immobilizing support.

10 Claims, 3 Drawing Sheets

```
                              3'-TTTCCTTCTTTCTCTCTTCTGATCA-biotin-5'
                                 ||||||||||||||||||||||||
    3'-GAATTCAGGAAGAAGAGGAAAGAGAAGAAAGGAAGAAAGAGAGAAGAT-5'
       ||||||||||||||||||||||||||||||||||||||||||||
    5'-TACTTAAGTCCTTCTTCTCCTTTCTCTTCTTTCCTTCTTTCTCTCTTC-3'
```

RAPID PURIFICATION OF CIRCULAR DNA BY TRIPLEX-MEDIATED AFFINITY CAPTURE

GOVERNMENT RIGHTS

This invention was made with government support under Contract Number DE-FG02-90ER61026 awarded by the U.S. Department of Energy. The government has certain rights in this invention.

This is a continuation of application Ser. No. 08/004,374 filed Jan. 14, 1993, abandoned.

FIELD OF THE INVENTION

The present invention relates to the field of DNA purification from bacterial lysates and in particular to the affinity purification of a supercoiled, double-stranded circular target DNA molecule using an immobilized oligonucleotide to form a local triple-helical region with a portion of the target DNA.

BACKGROUND OF THE INVENTION

DNA preparation and purification is essential to virtually all molecular biology. Most methods now in use for purifying double-stranded DNA from bacterial lysates rely on labor-intensive organic extractions and/or centrifugation. These techniques are not readily automated. Yet, as large-scale molecular biology projects such as the Human Genome Initiative move forward, automation of every phase of DNA analysis will become increasingly important.

In recent years, a new class of analytical and purification techniques have been developed which rely upon inherent biological affinities between proteins, between enzymes and their substrates, and between proteins and nucleic acids. Some affinity techniques exploit the exquisite specificity of monoclonal or polyclonal antibodies for particular counterpart antigens and haptens. In other techniques, target molecules are tagged with small molecules which are themselves the affinity target for other, more readily detectable or tangible molecules.

Affinity techniques are attractive because the desired molecules are rapidly and specifically immobilized away from the other contaminating molecules in an impure mixture, offering rapid and extensive purification or enrichment levels unachievable using classic techniques. Contaminating molecules are simply washed away, while target molecules remain firmly affinity-bound. Target molecules may be detached from their counterpart molecules simply by altering the environment to disfavor the affinity between the two. A second advantage of affinity purification techniques is that immobilization, detachment, and elution of target molecules are all relatively straightforward to automate.

Assays for particular DNA sequences are also performed based on DNA-DNA interactions. Typically, however, such interactions are based on the hybridization of a single-stranded DNA probe to a single stranded target DNA sequence. Hence, in a sample from a biological source, the normally double-stranded DNA must be denatured into a single-stranded state for the assay. This need for denaturing makes this hybridization technique unsuited for capture of double-stranded DNA.

What is lacking in the art is the ability to affinity-capture double-stranded DNA molecules using an immobilized nucleic acid. Since nucleic acids are easily synthesized, cloned, sequenced, and modified as desired, a nucleic acid affinity capture procedure is desirable.

SUMMARY OF THE INVENTION

The present invention is summarized in that double-stranded, supercoiled, circular target DNA containing a target sequence capable of forming a triple-helical structure may be purified rapidly from a bacterial cell lysate using a single-step affinity interaction between the target DNA and a single-stranded oligonucleotide probe. The two are drawn together under the conditions of the present method to reversibly form a triple-stranded structure. In the procedure, a target DNA molecule is rescued from the bacterial lysate after incubation of the lysate with a complex formed of a single-stranded duplex-binding oligonucleotide probe linked to an immobilizing support. The probe binds to the double-stranded target DNA forming a triple-stranded structure stabilized by Hoogsteen hydrogen bonds. Using the procedure, small bacterial cultures of approximately 1.5 ml can yield several µg of highly purified plasmid DNA, with no detectable RNA or chromosomal DNA contamination.

BRIEF DESCRIPTION OF THE DRAWINGS

FIG. 2 is a schematic representation of a pair of annealed oligonucleotides having a 40-base pair long complementary homopurine-homopyrimidine tract, and a schematic representation of an oligonucleotide constructed to bind to a portion of the homopurine-containing oligonucleotide.

DETAILED DESCRIPTION OF THE PREFERRED EMBODIMENT

Figure 1:
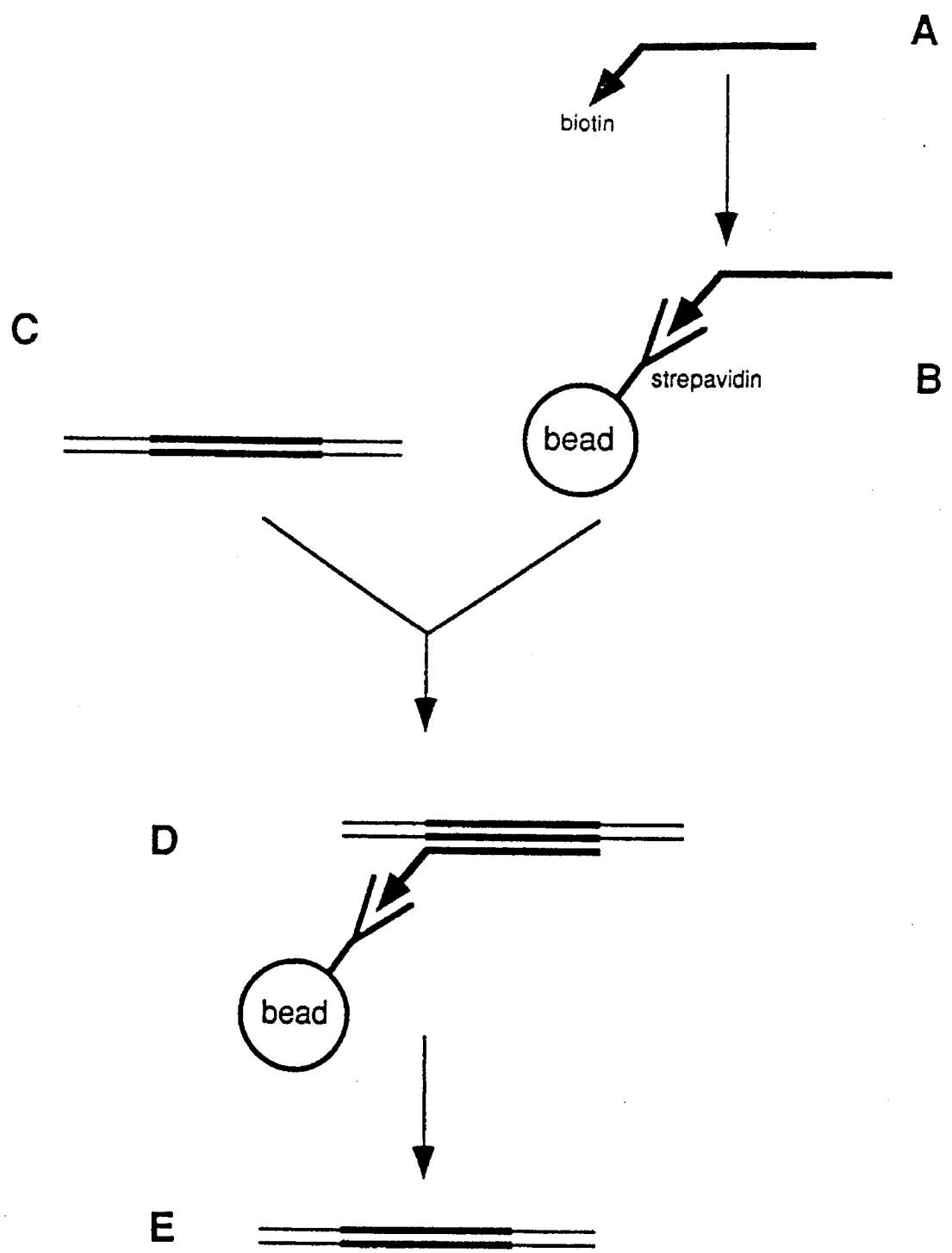
FIGS. 1A–1E are a schematic depiction of the triplex affinity capture method of the present invention.

The present invention is directed to a rapid method for capturing a circular, double-stranded target DNA molecule from a cleared bacterial lysate. The method exploits the propensity of a double-stranded circular DNA molecule (sometimes referred to hereinafter as a "duplex") having an appropriate target tract to form a three-stranded triple-helical structure (referred to hereinafter as a "triplex") with a single-stranded duplex-binding oligonucleotide probe designed to bind to the target tract. Triplex formation has been demonstrated in DNA molecules ranging in length from small plasmids to megabase chromosomes.

The unusual triplex structure is possible because the pyrimidine thymine (T) can recognize adenine-thymine (AT) base pairs to form T.AT triplets, and the pyrimidine cytosine (C) can recognize guanine-cytosine (GC) base pairs to form C.GC triplets. Protonated cytosine (C$^+$) has been found to have a higher affinity for duplex DNA than unprotonated cytosine. Protonated methylcytosine may also be utilized to form triplets, though it is not believed to significantly improve triplet formation at low pH. The purine guanine (G) has also been shown to form G.TA triplets with TA base pairs.

In this patent application, a circular duplex DNA molecule is a "target" if it contains a target tract that can form a triplex with a single-stranded duplex-binding oligonucleotide probe. Any circular duplex DNA molecule, such as a plasmid, cosmid or P1 cloning vector, containing a natural or engineered target tract may be a target DNA molecule.

In a preferred embodiment detailed in the example below, the target tract is a homopurine-homopyrimidine tract of a duplex DNA molecule and the probe is a single-stranded homopyrimidine designed to bind to the duplex homopurine strand. In triplexes formed between the two, the homopyrimidine probe is seated in the major groove parallel to the Watson-Crick purine strand and is held in place by Hoogsteen hydrogen bonds. However, the target tract of the present invention is not limited to such homopolymeric combinations. Instead, any probe-target combination having sufficient interactive ability to form a triplex via interstrand Hoogsteen hydrogen bonds under appropriate binding conditions is envisioned to be useful within the affinity capture method of the present invention.

For example, the invention may be practiced using a pyrimidine-rich probe formed of pyrimidines and purines. Such pyrimidine-rich probes do not interfere with triplex structure when directed to an appropriate target tract. For example, a G-residue in a pyrimidine-rich probe can recognize a TA base pair in the duplex target tract to form a G.TA triplet without disrupting the triplex.

Alternatively, a purine-rich probe, instead of a pyrimidine-rich probe, may be used to recognize a target tract having complementary purine-rich and pyrimidine-rich strands. In that case, the triplex forms with the probe strand sitting antiparallel to the target duplex Watson-Crick purine strand. Triplex formation with a purine-rich probe appears to be relatively pH-independent, yet is dependent upon the concentration of multivalent cations such as $Mg^{++}$ or spermine.

Furthermore, no exact complementarity between probe and target is required to practice the invention. By adjusting the triplex formation conditions to compensate for triplex-destabilizing mismatches, triplexes should form despite the presence of one or more mismatches between the target and probe sequences. It is believed that mismatched probes and targets can work sufficiently well to capture circular duplex target DNA molecules in accordance with the present invention, albeit under less stringent pH, temperature, and salt conditions than are used to bind perfectly complementary targets and probes.

In addition, the lengths of the probe and target may also vary from the lengths disclosed herein. The probe and the target need not be any particular length, though they must be sufficiently long (e.g., longer than about 15 nucleotides) to form a stable, hydrogen-bonded triplex. By varying the lengths of probes and targets, the triplex destabilizing effects of internal probe-target mismatches may also be offset. It is expected that longer probes and targets will bind more readily than will shorter probes and targets, and, further, that longer probes and targets will form triplexes under conditions of higher stringency than shorter ones.

The method of the present invention is presented schematically in FIG. 1. The single-stranded, duplex-binding oligonucleotide, immobilized onto a readily-isolated solid-phase support, acts as a probe onto which the target tract of the target DNA molecule will attach under appropriate binding conditions. FIGS. 1 (A) and (B) depict the preparation and immobilization of the single-stranded oligonucleotide probe. In FIG. 1 (A), the oligonucleotide, which may be synthesized using standard synthetic procedures, is shown as a 5' biotinylated molecule, although 3' or internal biotinylation is also possible. In FIG. 1 (B), the biotinylated oligonucleotide is coupled to a streptavidin-coated immobilizing support, shown as a magnetic bead, to form a complex referred to hereinafter as a triplex capture complex.

The non-covalent biotin-streptavidin attraction is strong enough ($K_d=10^{-15}$ [M]) to secure the triplex capture complex together.

The invention, however, is not limited to the preferred streptavidin-biotin linkage. Any linkage, including covalent linkages, that can join a duplex-binding oligonucleotide probe to an immobilizing support useful within the capture process of the present invention would be sufficient.

Neither is the invention limited to a particular form of immobilizing support. Although the present inventors have found streptavidin-coated magnetic beads to be a particularly desirable support for biotin-labelled duplex-binding probe, it is envisioned that any support that can be retrieved after triplex formation and that is capable of immobilizing and displaying an attached duplex-binding probe for affinity capture would be adequate. For example, a duplex-binding probe could be immobilized on a column packing material or on a filter paper support.

The triplex capture complex described above is useful for isolating target DNA molecules in a single binding step insofar as it contains in one aspect a probe for a circular duplex target DNA, and in a second aspect a solid support that permits the bound target to be easily retrieved from the bacterial lysate, as described below.

FIG. 1 (C) depicts the mixture of the triplex capture complex with the bacterial lysate. At the left side of FIG. 1 (C), a portion of a target DNA molecule, resident in the lysate, is shown. The target tract is depicted in thicker lines than the remainder of the DNA. FIG. 1 (D) shows a single-step affinity capture of DNA by triplex formation. After a brief incubation of the triplex capture complex in the bacterial lysate under triplex-forming conditions, a new complex, held together by the triplex, is created between the triplex capture complex and the target DNA. The immobilizing solid support of the triplex capture complex and the bound target DNA are then segregated away from the liquid lysate. In the case of a magnetic bead support, a magnet may be used to isolate the triplex capture complex and bound target DNA while the lysate is drawn off. If the support is in filter form, it may simply be removed from the lysate.

Next, contaminating material is washed from the bound DNA complex using a washing buffer that does not disturb the triplex. The target DNA is then eluted from the oligonucleotide, as shown in FIG. 1 (E), using a high-pH, low ionic strength elution buffer that causes the probe to disengage from the target tract, destroying the triplex. The low ionic strength permits the purified target DNA to be used directly in cloning, sequencing or other techniques.

Using this basic concept, any circular, double-stranded DNA molecule having the target tract in its sequence may be captured by triplex affinity capture using an appropriate oligonucleotide probe. Having generally described the basic concept of the present invention, what follows is a detailed description of the process of the present invention and of the components useful in the process.

As noted, a target DNA molecule, such as a cloning vector, useful in the method of the present invention must include in its sequence a double-stranded target tract that can, under appropriate reaction conditions, form a triplex with a single-stranded duplex-binding oligonucleotide. A suitable target tract may be formed by annealing a pair of synthesized complementary oligonucleotides. Preferably, the 5' and 3' termini of the two oligonucleotides are designed so that the resulting double-stranded annealed oligonucleotide may be ligated into a restriction enzyme site. To facilitate the cloning process, the termini of the annealed double-stranded oligonucleotide should complement the restriction enzyme site into which the oligonucleotide will be ligated. The annealed double-stranded oligonucleotide ends may terminate in a 5' overhang, 3' overhang, blunt end, or a combination of the above. It is also preferable not to regenerate the restriction enzyme site into which the target tract is cloned, thereby providing an easy means for preventing insert-lacking cloning vectors from being successfully transformed into bacteria. To reduce the background of insert-lacking transformants, the transforming DNA may simply be cleaved with the original cloning enzyme, thereby linearizing those DNA molecules that lack inserts. Linear vectors transferred into bacteria are not maintained after transformation at an appreciable frequency.

To form a target DNA molecule, the target tract may be ligated into any cloning vector having a site into which tract may be cloned. As an alternative, an existing target tract of known sequence could be excised from its host for transfer into a desired gene transfer vector. An appropriate target tract might also already be present in a vector, by design or by coincidence. Regardless of the method for producing a target cloning vector, the vector would preferably include such useful elements as a polylinker, a selectable marker, and a marker that visually or biochemically distinguishes insert-containing transformants from transformants that have received only the cloning vector. The pUC series of cloning vectors are preferred recipients of an annealed oligonucleotide target tract. In particular, pUC19 with its ampicillin resistance gene, blue-white marker system for insert containing transformants, and polylinker is especially preferred.

To carry out the capture method, small (e.g., 1.5 ml) cultures of a bacterial transformant cells containing a target DNA molecule are grown overnight and harvested by microcentrifugation. The cell pellet is resuspended in an alkaline lysis buffer. The resuspended cells are lysed by adding a NaOH/SDS solution and incubating on ice for 5 minutes. The lysis is terminated by adding acidic potassium acetate (pH 5.0) to approximately 1M. While cell lysis conditions are well known and are not intended to limit the present invention, the cell lysate should have a pH<7 before the triplex capture procedure of the present invention is begun. Target DNA capture is preferably performed in an acidic environment, to promote the protonation of cytosine residues in the duplex-binding probe. Protonated cytosines form triplets more readily than unprotonated cytosines. The affinity of a duplex-binding probe for its target may increase if the cytosine residues are methylated, though this is not essential. Binding can be carried out in 1M potassium acetate, pH 5.0.

The triplex capture complex described above is added to the acidic lysate and is incubated at room temperature for a sufficient length of time to form triplexes between the complex and the target DNA molecules in the lysate. To expedite the process, the incubation is preferably short, on the order of 15 minutes.

After target DNA capture, the triplex capture complex with its bound target DNA is recovered from the lysate, in a manner appropriate to the nature of the immobilizing support. For instance, if the immobilizing support is magnetic, the complex may be localized in its vessel by magnetic force and contaminating material in the lysate may be pipetted away. If the support is a filter paper-type product, the paper itself may simply be removed from the lysate.

Residual unbound DNA and other contaminants are washed away from the immobilized complex, preferably first in a buffer that reinforces triplex binding, such as 1M potassium acetate, then in a washing buffer, such as 10 mM sodium acetate, pH 5.8, 100 mM $MgCl_2$. Finally, the target DNA, free of contaminating material, is eluted from the complex in a triplex destabilizing basic, low ionic strength solution such as 50 mM Tris-HCl, pH 9.0.

EXAMPLE

A pair of 48 base long complementary oligonucleotides, depicted in FIG. 2, were synthesized and were annealed to form a target tract useful in the creation of a target DNA molecule that can be rescued by the method of the present invention. All oligonucleotides described herein were synthesized on an Applied Biosystems 381A DNA synthesizer (Foster City, Calif.) and were purified by reversed-phase high performance liquid chromatography or by passage through a Sep-Pak C18 cartridge (Waters, Milford, Mass.). The concentration of each purified oligonucleotide was determined by spectrophotometry.

The first 48-mer, shown as the bottom strand in FIG. 2 and attached hereto as SEQ ID:1, contained a 40-base homopyrimidine sequence. The second 48-mer, shown as the middle strand in FIG. 2 and attached hereto as SEQ ID:2, contained a 40-base homopurine sequence, complementary to the homopyrimidine sequence of the first 48-mer. The double-stranded 40-base pair long complementary region generated after annealing is referred to in this example as the homopurine-homopyrimidine tract. The 5'-terminal TA dinucleotide overhang on each end of the annealed double-stranded oligonucleotide was designed to facilitate cloning into a restriction enzyme site having a AT dinucleotide 3' overhang, such as a site generated by digestion with NdeI.

Figure 3:
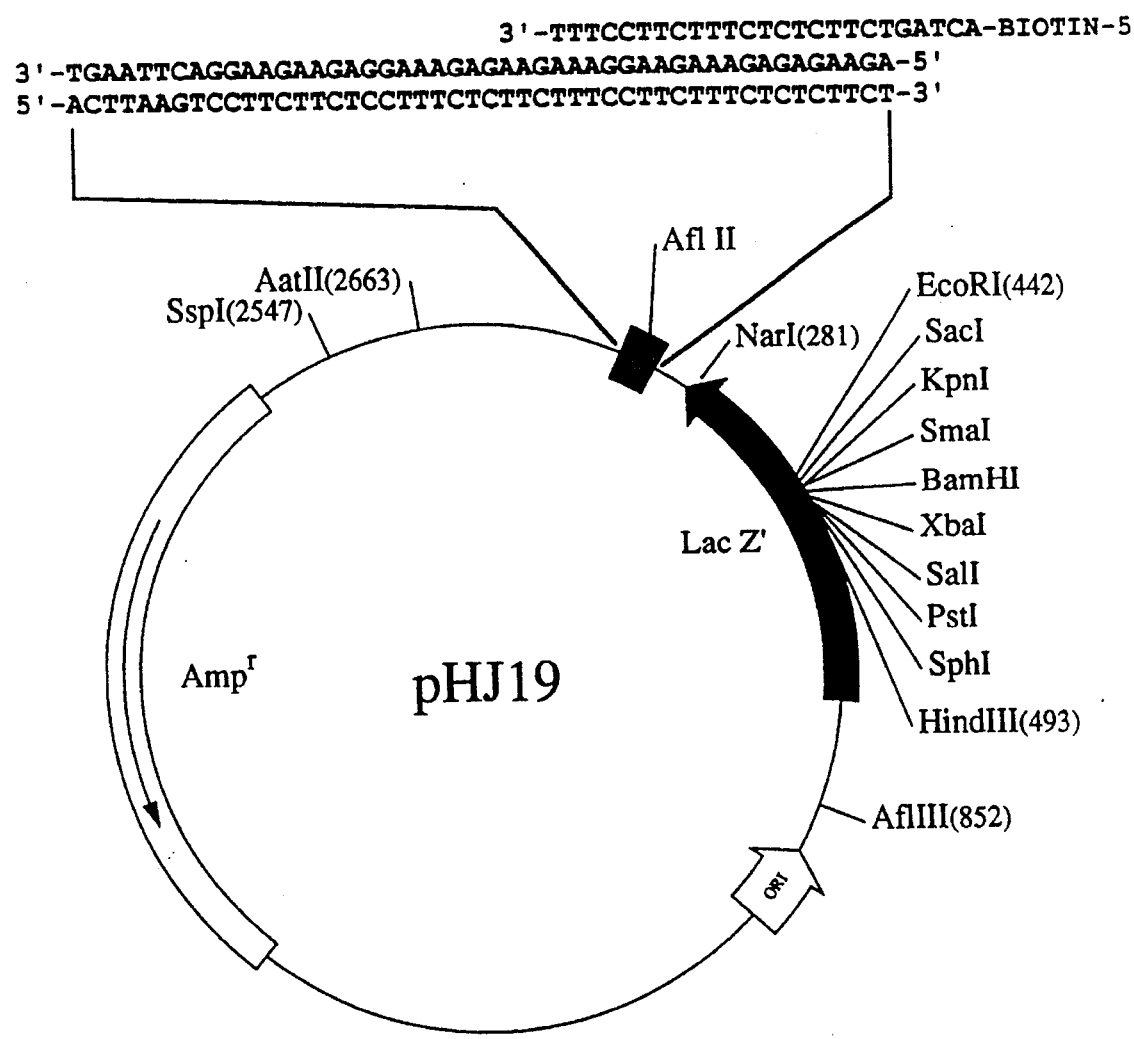
FIG. 3 depicts the plasmid cloning vector pHJ19 which includes the double-stranded homopurine-homopyrimidine tract of FIG. 2.

FIG. 3 depicts pHJ19, a cloning vector useful as a target DNA molecule in the capture scheme of the present invention. pHJ19 is a pUC19-derivative vector having the homopurine-homopyrimidine tract of FIG. 2 inserted into its NdeI restriction enzyme digestion site (CATATG). pHJ19 has been used by the inventors as a recipient for foreign genes which may then be rescued using the method of the present invention, as described below. The pHJ19 vector has been shown to facilitate the capture of fragments of various sizes indicating its utility as a general purpose cloning vector useful in the triplex affinity capture scheme of the present invention. Note that ligation of the homopurine-homopyrimidine tract into the NdeI site does not regenerate the NdeI site, although an adjacent AT base pair left in the pHJ19 vector after the Nde I cleavage and ligation provides an additional base pair to the triplex-forming region of the vector, making a total length of 20 bases for the triplex-forming region.

An oligonucleotide probe determined by the inventors to stably form a homopyrimidine-homopurine-homopyrimidine triplex with the homopurine-homopyrimidine target tract is shown as the top strand in FIGS. 2 and 3, and is attached as SEQ ID:3. The 25-base-long oligomer includes a homopyrimidine portion that is complementary to the 20 3'-most nucleotides of the homopurine strand of the annealed homopurine-homopyrimidine tract resident in pHJ19. The single-stranded oligonucleotide of FIG. 2 was tagged at its 5' end with a biotin molecule in a standard synthetic procedure using biotin phosphoramidite (Glen Research, Sterling, Va.) as the biotin source.

To form the triplex capture complex, the biotin-labeled oligonucleotide was immobilized on streptavidin-coated magnetic beads (Dynabeads M-280, Dynal, Inc., Great Neck, N.Y,). These commercially available beads were reported to possess 0.3 pmoles of biotin-binding sites per μg of beads. 100 μl (1 mg) of the magnetic beads were washed twice with phosphate-buffered saline (PBS; 0.15M NaCl, 10 mM sodium phosphate, pH 7.5). 20 pmol of biotinylated oligonucleotide was added to the beads and the mixture was kept at room temperature until the streptavidin-coated magnetic beads and the biotinylated single-stranded oligonucleotide formed the triplex capture complexes, preferably kept at room temperature for at least 15 minutes. The supernatant was removed and the triplex capture complexes were washed twice sequentially with PBS, elution buffer (50 mM Tris-HCl, pH 9.0), and binding buffer (1M potassium acetate, pH 5.0).

The triplex capture complexes were stable in PBS at 4° C. for at least 2 months without observable degradation and have been shown to be reusable at least 10 times to capture target vectors without observable decrease in performance. To regenerate the beads after each use, they were washed twice sequentially with 1.0M Tris-HCl, pH 9.0, binding buffer and PBS, and were then stored at 4° C.

The triplex capture complexes were used to capture pHJ19 target DNA from a mixture of heterogeneous DNA molecules in a process that began with cell lysis of small preparations of bacteria containing copies of the target vector. The bacterial cells were pelleted in a microcentrifuge and were resuspended fully in 100 μl of 50 mM glucose, 10 mM EDTA, 25 mM Tris-HCl, pH 8.0. The bacterial cells were lysed by treatment with 200 μl of 0.2M NaOH/1% SDS followed by incubation on ice for 5 minutes and neutralization with 150 μl of 3M potassium acetate, pH 5.0. The high salt concentration of the potassium acetate precipitated denatured proteins, chromosomal DNA, cellular debris and SDS, leaving supercoiled plasmid DNA in solution with contaminating RNAs, residual chromosomal DNA and proteins, polysaccharides, and metabolites. The precipitated components were removed by high-speed microcentrifugation to leave an acidic cleared lysate.

The triplex capture complexes, incubated for 15 minutes in the cleared lysate, specifically formed a triplex with the target plasmid DNA molecules. The acidic environment of the cleared lysate encouraged formation of a stable triplex, in that triplexes formed more readily when the cytosine residues of the single-stranded oligonucleotide were protonated.

The triplex, captured by the oligonucleotide probe and bound to the magnetic beads via the streptavidin-biotin linkage, was separated from the lysate using a magnet and was washed sequentially with 100 μl of binding buffer and 100 μl of washing buffer (10 mM sodium acetate, pH 5.8, 100 mM $MgCl_2$) to eliminate remaining unbound cellular material. The liquid was carefully pipetted away after each wash step.

The target DNA was eluted from the triplex capture complexes by a 10 minute incubation in elution buffer, the basic pH of which (pH=9.0) disrupts the triple-helical structure, leaving the double-stranded DNA intact. Because of the wide variety of applications which require purified DNA, the concentration of Tris-HCl in the elution buffer was kept as low as possible while still remaining effective, in order to eliminate a subsequent desalting step that would have been required before further use. The double-stranded target DNA remained in the supernatant and was used directly for restriction enzyme digestion, cloning, gel electrophoresis, and as a DNA sequencing template.

The triplex affinity capture scheme of the present invention is preferably used to capture supercoiled circular plasmid DNAs from cell lysates. Although the present method will capture linearized DNA or other linear DNA molecules, the extra effort necessary to both extract and to digest supercoiled plasmid DNA is not necessary. The capture of supercoiled double-stranded pHJ19 DNA was approximately 4 times more efficient than the capture of linearized pHJ19 DNA (80% recovery vs. 20%) under the capture conditions reported herein.

The entire capture and recovery process described above can be accomplished in under 30 minutes, yielding DNA that may be used directly in subsequent molecular-biological processes.

---

We claim:

1. A process for quickly and efficiently purifying circular DNA from a bacterial host, consisting essentially of the steps of:
    a) creating a cleared cell lyeate from a culture of bacterial cells having therewithin a double-stranded, circular target DNA molecule in a mixture with other heterogeneous circular DNA molecules, the target DNA molecule containing a target tract appropriate for triple helix formation, the target tract containing non-identical homopurine bases on one strand;
    b) adding to the cleared lysate a triplex capture complex including an immobilizing support and an oligonucleotide probe able to form a triplex with the target tract, the support and the probe being bound together, the probe containing non-identical homopyrimidine bases;
    c) incubating the triplex capture complex in the cleared cell lysate on the order of 15 minutes under acidic conditions under conditions such that the triplex capture complex and the double-stranded circular DNA molecule including the target DNA will form a complex, the triplex capture complex and the target DNA being held together by a triplex formed between the probe and the target tract;
    d) separating the triplex capture complex-target DNA complex from the cell lysate, any other DNA, and from any other contaminants by separating the immobilizing support from the cleared lysate;
    e) disrupting the triplex by raising the pH of the triplex capture-target DNA complex; and
    f) the target DNA from the triplex capture complex and recovering the target double-stranded circular target DNA, wherein steps b–f are performed within 30 minutes.

2. A process for purifying circular DNA as claimed in claim 1 wherein the target tract comprises the following DNA sequence, also contained in SEQ ID NO. 1 and SEQ ID NO. 2:

5'-TCCTTCTTCTCCTTTCTCTTCTTTCCT-
TCTTTCTCTCTTC-3'
3'-AGGAAGAAGAGGAAAGAGAAGAAAGGAA-
GAAAGAGAGAAG-5'.

3. A process for purifying circular DNA as claimed in claim 1 wherein the oligonucleotide probe comprises the following DNA sequence, also bases 7 to 25 of SEQ ID NO. 3:

5'-CTTCTCTCTTTCTTCCTTT-3'.

4. A process for purifying circular DNA as claimed in claim 1 wherein the cell lysate is made acidic with potassium acetate, pH 5.0.

5. A process for purifying circular DNA as claimed in claim 1 wherein the immobilizing support is a streptavidin-coated magnetic bead and the oligonucleotide is biotin-labelled, and wherein the magnetic bead and the oligonucleotide are bound together by an interaction between streptavidin and biotin.

6. A process for purifying circular DNA as claimed in claim 5 further including a step of immobilizing the immobilizing support using a magnet to attract the magnetic beads.

7. A process for purifying circular DNA as claimed in claim 5 wherein the triplex capture complex is provided by keeping the streptavidin-coated magnetic bead and the biotin-labelled oligonucleotide at room temperature until the triplex capture complex is formed.

8. A process for purifying circular DNA as claimed in claim 1 wherein the disrupting step is performed under basic conditions.

9. A process for purifying circular DNA as claimed in claim 7 wherein the basic conditions are provided by 50 mM; Tris-HCl, pH 9.0.

10. A process for quickly and efficiently purifying circular DNA from a bacterial host, comprising the steps of:
    a) creating a cleared cell lysate from a culture of bacterial cells having therewithin a double-stranded, circular target DNA molecule in a mixture with other heterogeneous circular DNA molecules, the target DNA molecule containing a target tract appropriate for triple helix formation, the target tract containing non-identical homopurine bases on one strand;
    b) adding to the cleared lysate a triplex capture complex including an immobilizing support and an oligonucleotide probe able to form a triplex with the target tract, the support and the probe being bound together, the probe containing non-identical homopyrimidine bases;

c) incubating the triplex capture complex in the cleared cell lysate on the order of 15 minutes under acidic conditions under conditions such that the triplex capture complex and the double-stranded circular DNA molecule including the target DNA will form a complex, the triplex capture complex and the target DNA being held together by a triplex formed between the probe and the target tract;

d) separating the triplex capture complex-target DNA complex from the cell lysate, any other DNA, and from any other contaminants by separating the immobilizing support from the cleared lysate;

e) disrupting the triplex by raising the pH of the triplex capture-target DNA complex; and f) separating the target DNA from the triplex capture complex and recovering the target double-stranded circular target DNA, wherein steps b–f are performed within 30 minutes.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:1:

TACTTAAGTC    CTTCTTCTCC    TTTCTCTTCT    TTCCTTCTTT    CTCTCTTC    48

( 2 ) INFORMATION FOR SEQ ID NO:2:

( i ) SEQUENCE CHARACTERISTICS:

(A) LENGTH: 48 base pairs
(B) TYPE: nucleic acid
(C) STRANDEDNESS: single
(D) TOPOLOGY: linear (iii) HYPOTHETICAL: NO (iv) ANTI-SENSE: NO (xi) SEQUENCE DESCRIPTION: SEQ ID NO:2:

TAGAAGAGAG AAAGAAGGAA AGAAGAGAAA GGAGAAGAAG GACTTAAG    48

(2) INFORMATION FOR SEQ ID NO:3:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:3:

ACTAGTCTTC TCTCTTTCTT CCTTT    25